United States Patent [19]
Groziak

[11] Patent Number: 6,083,936
[45] Date of Patent: Jul. 4, 2000

[54] BORON HETEROCYCLE STEROID MIMICS AND ASSOCIATED PHARMACEUTICAL COMPOSITIONS AND METHODS OF USE

[75] Inventor: Michael P. Groziak, Palo Alto, Calif.

[73] Assignee: SRI International, Menlo Park, Calif.

[21] Appl. No.: 09/236,948

[22] Filed: Jan. 25, 1999

[51] Int. Cl.[7] ............................ A01N 55/58; C07C 69/96; C07F 5/04; C07F 5/02
[52] U.S. Cl. ............................ 514/64; 558/269; 558/289; 564/11
[58] Field of Search ................................ 558/269, 289; 514/64; 564/11

[56] References Cited

U.S. PATENT DOCUMENTS

| | | | |
|---|---|---|---|
| 5,144,026 | 9/1992 | Gabel | 540/500 |
| 5,362,732 | 11/1994 | Spielvogel et al. | 514/256 |
| 5,599,796 | 2/1997 | Schinazi et al. | 514/44 |
| 5,612,017 | 3/1997 | Miura et al. | 424/161 |
| 5,648,532 | 7/1997 | Hawthorne et al. | 564/8 |

OTHER PUBLICATIONS

Groziak et al., Boron Heterocycles Bearing a Peripheral Resemblance to Naturally–Occurring Purines: . . . , *J. Am. Chem. Soc.*, vol. 116, No. 17, Dec. 1994.

Barsony et al. (1995), "Development of a Biologically Active Fluorescent–labeled Calcitriol and its Use to Study Hormone Binding to the Vitamin D Receptor," *Analytical Biochem.* 229:68–79.

French et al. (1993), "A Synthesis of 7α–substituted Estradiols: Synthesis and Biological Evaluation of a 7α–pentyl–substituted Bodipy Fluorescent Conjugate and a Fluorine–18–labeled 7α–pentylestradiol Analog," *Steroids* 58:157–169.

Groziak et al. (1994), "Boron Heterocycles Bearing a Peripheral Resemblance to Naturally–Occurring Purines: Design, Syntheses, Structures and Properties," *J. Am. Chem. Soc. 116*:7597–7605.

Groziak et al. (1997), "Planar Boron Heterocycles with Nucleic Acid–Like Hydrogen–Bonding Motifs," *J. Am. Chem. Soc. 119*:7817–7826.

Kabalka et al. (1997), "The Role of Boron MRI in Boron Neutron Capture Therapy," *J. Neuro–Oncol. 33*: 153–161.

Kabalka et al. (1988), "Boron–11 MRI and MRS of Intact Animals Infused With a Boron Neutron Capture Agent," *Magnetic Resonan. Med. 8*: 231–237.

Robinson et al. (1998), "A 2–Alkyl Substituted 2,3,1–Benzodiazaborane," *J. Acta Crystallogr. C54*:71–73.

Sweet (1981), "Boron Estrogens: Synthesis, Biochemical and Biological Testing of Estrone and Estradiol–17β, 3–carboranylmethyl Ethers," *Steroids 37*:223–238.

Wellmann et al. (1991), "Synthesis and Biological Behavior of a Boronated Analogue of the Antiestrogen U 23, 469–m," *Z. Naturforsch [C] 46*:252–256.

Bailey et al. (1980), "Boron–Containing Antibacterial Agents: Effects on Growth and Morphology of Bacteria Under Various Culture Conditions," *Antimicrobial Agents and Chem.17*(4):549–553.

Baldock et al. (1996), "A Mechanism of Drug Action Revealed by Structural Studies of Enoyl Reductase," *Science 274*:2107–2110.

Grassberger et al. (1984), "Preparation and Antibacterial Activities of New 1,2,3–Diazaborine Derivatives and Analogues," *J. Med. Chem. 27*:947–953.

*Primary Examiner*—Joseph McKane
*Assistant Examiner*—Dominic Keating
*Attorney, Agent, or Firm*—Dianne E. Reed; Reed & Associates

[57] ABSTRACT

Boron heterocycle steroid mimics are provided that are useful as pharmaceutical agents, particularly in the treatment of estrogen-dependent disorders such as estrogen-dependent cancers. The compounds are also useful in diagnostic techniques such as magnetic resonance imaging (MRI) and magnetic resonance spectroscopy (MRS), in boron neutron capture therapy, and in fluorescence emission-based modalities. Pharmaceutical formulations and methods of using the novel compounds are provided as well.

26 Claims, 1 Drawing Sheet

BORON HETEROCYCLE STEROID MIMICS AND ASSOCIATED PHARMACEUTICAL COMPOSITIONS AND METHODS OF USE

TECHNICAL FIELD

The present invention relates generally to pharmaceuticals, and more particularly relates to novel pharmaceutical agents in the form of boron heterocycle steroid mimics. The invention additionally relates to pharmaceutical compositions containing a compound of the invention, and to methods for using the novel compounds as therapeutic and diagnostic agents.

BACKGROUND

Despite continuing research on breast cancer chemotherapy, almost all of the chemotherapeutic agents currently used to treat breast cancer still fall into just two categories: modified steroids (framework A); and compounds related to diethylstilbestrol (framework B).

Framework "A":

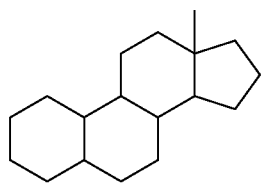

Examples of "A"-Type Chemotherapeutic Agents:

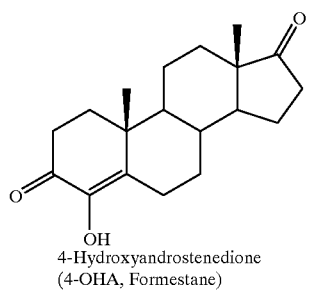

4-Hydroxyandrostenedione
(4-OHA, Formestane)

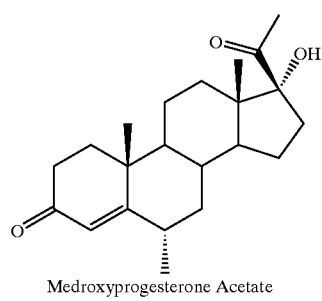

Medroxyprogesterone Acetate

-continued

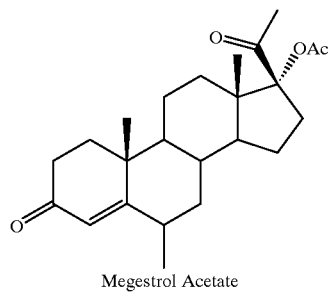

Megestrol Acetate

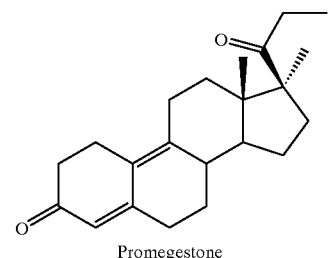

Promegestone

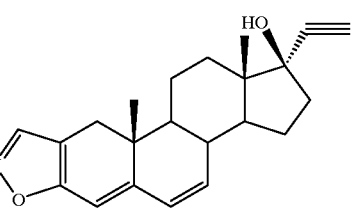

Danazol

Framework "B":

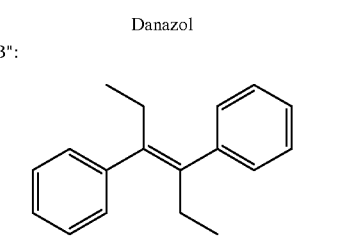

Examples of "B"-Type Chemotherapeutic Agents:

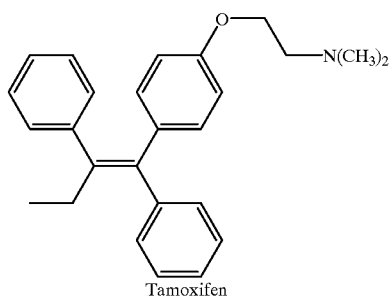

Tamoxifen

-continued

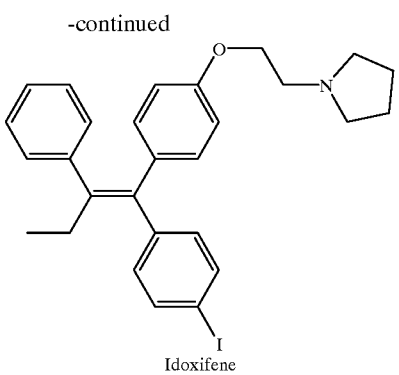
Idoxifene

The best agents currently in clinical use are not significantly more effective than the 30-year-old antiestrogen tamoxifen (Nolvadex®), shown above, or the first generation aromatase inhibitors. Furthermore, toxic side effects and the emergence of drug resistance continue to be problematic. It is accordingly critical that new molecular platforms be developed for the development of new, highly effective agents useful in breast cancer chemotherapy. The present invention is addressed to this timely and urgent need in the art.

The invention provides an entirely new class of compounds that are structural mimics of the two principal natural estrogens, estradiol and estrone, but are otherwise unlike any pharmaceutical agents known to date. The novel compounds are boron heterocycles that effectively inhibit human breast cancer cell growth either by blocking the estrogen-receptor-dependent growth signal, by inhibiting an estrogen-producing enzyme, or both. The compounds are also advantageous insofar as the boron atom within the molecular structure enables use in $^{11}$B nuclear magnetic resonance and magnetic resonance imaging. The novel boron-based estrogen mimics are additionally useful in boron neutron capture therapy for treating a variety of tumor types, including breast cancer. Further, those compounds of the invention that are fluorescent can be used in diagnostic procedures involving fluorescence emission spectroscopy, as will be appreciated by those skilled in the art.

Carbone derivatives of estrogens are described in Sweet (1981), "Boron Estrogens: Synthesis, Biochemical and Biological Testing of Estrone and Estradiol-17β, 3-carboranylmethyl Ethers,"*Steroids* 37:223–238, where the derivative was shown to have a low affinity for the estrogen receptor of only 0.5 compared with a value of 100 for estradiol-17β. Wellmann et al. (1991), "Synthesis and Biological Behavior of a Boronated Analogue of the Antiestrogen U 23,469-m,"*Z. Naturforsch* [C]46:252–256, concludes that the boronated analogue has a large, non-specific uptake in ZR 75-1 breast cancer cells, but does not accumulate at high enough level in cells to have any therapeutic effect following thermal neutron irradiation. There is some description in the literature concerning boron heterocycles as potential pharmaceutical agents. For example, Groziak et al. (1994), "Boron Heterocycles Bearing a Peripheral Resemblance to Naturally-Occurring Purines: Design, Syntheses, Structures and Properties,"*J Am. Chem. Soc.* 116:7597–7605, discloses boron-containing purine-like heterocycles as potentially useful bioactive agents. Groziak et al. (1997), "Planar Boron Heterocycles with Nucleic Acid-Like Hydrogen-Bonding Motifs,"*J Am. Chem. Soc.* 119:7817–7826, pertains to similar boron-containing compounds. Robinson et al. (1998), "A 2-Alkyl Substituted 2,3,1-Benzodiazaborane,"*J Acta Crystallogr.* C54:71–73, relates structural information pertaining to a benzodiazaborane, specifically 1,2-dihydro-1-hydroxy-2-methyl-2,3,1-benzodiazaborine. Still other references describe 2,3,1-benzodiazaborines as antibacterial agents; see, e.g., Baldock et al. (1996), "A Mechanism of Drug Action Revealed by Structural Studies of Enoyl Reductase," *Science* 274:2107–2110; Grassberger et al. (1984), "Preparation and Antibacterial Activities of New 1,2,3-Diazaborine Derivatives and Analogs,"*J Med. Chem.* 27:947–953; and Bailey et al., "Boron-Containing Antibacterial Agents: Effects on Growth and Morphology of Bacteria Under Various Culture Conditions,"*J Antimicrob. Agents Chemother.* 17:549–553.

Boron-containing compounds have been used in boron neutron capture therapy (BNCT). BNCT is an anti-cancer bimodal radiation therapy utilizing a radiosensitizing compound that contains a stable boron-10 isotope and nonionizing neutron radiation. The patient is first administered the boron-containing compound that is preferably although not necessarily enriched in boron-10 isotope. In the second step, the tumor area is irradiated with thermal neutrons. Some of the neutrons are captured by boron-10 in the tumor and a nuclear reaction occurs that results in the production of helium nuclei (α-particle), lithium nuclei, and about 100 million times more energy that the initial irradiated energy. The generated energy destroys malignant cells containing the boron compounds. Selectivity is thus achieved through the use of compounds which accumulate primarily in malignant cells and/or by aiming the neutron beam at the tumor mass which contains the boron carrier. U.S. Pat. No. 5,599,796 to Schinazi et al. describes boron-containing anti-sense oligonucleotides for BCNT targeting urogenital cancer cells, while U.S. Pat. No. 5,362,732 to Spielvogel et al. describes boronate purine and pyrimidine bases and phosphate esters for use in BNCT. U.S. Pat. No. 5,612,017 to Miura et al. describes a dimeric halogenated sulfidohydroborane compound for BNCT, and U.S. Pat. No. 5,648,532 to Hawthorne et al. describes boron salts encapsulated with liposomes for use in BNCT.

The concentration of boron-10 within the tissues of patients to whom boron-containing compounds have been administered has been estimated by extrapolation from the concentration of boron-10 in blood and tissue samples. These indirect extrapolations, however, are approximate, and a more accurate method of determining the concentration and distribution of boron-10 in a patient being prepared for BNCT is needed. Multinuclear magnetic resonance imaging (MRI) and spectroscopy (MRS) are potentially valuable for evaluation of BNCT agents since boron-10 and boron-11 are magnetically active. Kabalka et al. (1988), "Boron-11 MRI and MRS of Intact Animals Infused With a Boron Neutron Capture Agent,"*Magnetic Resonan. Med.* 8: 231–237, describe the use of cesium μ-disulfido-bis (undecahydro-closo-dodecaborate) in imaging experiments with rats, while the use of the compound in imaging mammals is described in Kabalka et al. (1997), *J. Neuro-Oncol.* 33: 153–161. In addition, French et al. (1993), "A Synthesis of 7α-substituted Estradiols: Synthesis and Biological Evaluation of a 7α-pentyl-substituted Bodipy Fluorescent Conjugate and a Fluorine-18-labeled 7α-pentylestradiol Analog,"*Steroids* 58:157–169, describes the conjugation of a BODIPY fluorophore with an estradiol as a fluorescent probe for the estrogen receptor, while Barsony et al. (1995), "Development of a Biologically Active Fluorescent-labeled Calcitriol and its Use to Study Hormone Binding to the Vitamin D Receptor," disclose the conjugation of a BODIPY fluorophore to calcitriol derivatives as a fluorescent probe for vitamin D receptor.

The use of boron heterocycles as provided herein, however, is believed to be new and completely unsuggested by the art. That is, no art of which applicants are aware discloses the boron heterocycle steroid mimics for the treatment of cancer or for any other purpose, either therapeutic or diagnostic.

SUMMARY OF THE INVENTION

Accordingly, it is a primary object of the invention to address the above-described need in the art by providing novel compounds useful as chemotherapeutic agents, particularly in the treatment of breast cancer.

It is another object of the invention to provide such compounds in the form of boron heterocycle steroid mimics.

It is an additional object of the invention to provide pharmaceutical compositions containing one or more of the novel compounds as an active agent.

It is still another object of the invention to provide a method for treating an estrogen-dependent disorder by administering a compound of the invention to an individual suffering from such a disorder.

It is yet another object of the invention to provide such a method wherein the estrogen-dependent disorder is breast cancer.

It is a further object of the invention to provide a method for using the present compounds in diagnostic techniques, such as magnetic resonance imaging (NI) and magnetic resonance spectroscopy (MRS).

It is still a further object of the invention to provide a method for using a compound of the invention in boron neutron capture therapy to treat a cancer patient.

It is yet a further object of the invention to provide a method for using a compound of the invention in fluorescence emission-based modalities.

Additional objects, advantages and novel features of the invention will be set forth in part in the description which follows, and in part will become apparent to those skilled in the art upon examination of the following, or may be learned by practice of the invention.

In one embodiment of the invention, then, a novel compound is provided having the structural formula (I)

(I)

wherein:
 a, b, c and d represent optional double bonds;
 e represents an optional single bond;
 m and n are independently 0 or 1, with the proviso that if d is present as a double bond, one of m and n is 0;
 $R^1$ is H, carbonyl, methylene or mono(lower alkyl)-substituted methylene, wherein, when carbonyl, methylene or mono(lower alkyl)-substituted methylene, $R^1$ is directly and covalently bound to Y;
 $R^2$ is selected from the group consisting of H, lower alkyl, lower acyl, phenyl, benzyl, —C(O)-aryl and —$SO_2NH_2$;
 $R^3$ is H or lower alkyl;
 $R^4$ is selected from the group consisting of H, methoxy, halogen, cyano, —$CH_2CH=CH_2$, —CHO, —$NR^9R^{10}$ and —$(CH_2)NR^9R^{10}$ wherein $R^9$ and $R^{10}$ are independently H or lower alkyl;
 $R^5$ is selected from the group consisting of H, halogen, —$NO_2$, —CHO, —$CH_2CH=CH_2$, —$NR^9R^{10}$ and —$(CH_2)NR^9R^1$ wherein $R^9$ and $R^{10}$ are independently H or lower alkyl;
 $R^6$ is selected from the group consisting of H, hydroxyl, —$OR^{11}$ and —$SR^{11}$ wherein $R^{11}$ is lower alkyl, lower acyl or aryl;
 one of $R^7$ and $R^8$ is H and the other is H, alkyl, alkenyl, alkynyl, alkoxy, acyl or acyloxy, or one of $R^7$ and $R^8$ is hydroxyl and the other is H, alkyl, alkenyl, alkynyl, acyl, or $R^7$ and $R^8$ together form =O;
 X is N, CH or $CR^{12}$ wherein $R^{12}$ is alkyl, aryl, —O-alkyl, —O-aryl, —S-alkyl or —S-aryl;
 Y is N, NH, C or CH, and is optionally bound directly and covalently to $R^1$;
 W is O, S, N or C, with the provisos that (1) if W is O or S, then d is absent and both m and n are 0, and (2) if W is N, then either (a) d is absent and one but not both of m and n is 0 or (b) d is present and m and n are both 0;
 when e is present, Z is N, 0, S, CH or $CH_2$, with the proviso that W and Z are not both O and S, and L is $CH_2$, $CH_2$—$CH_2$, CH=CH or NH; and
 when e is absent, Z is NH, $NH_2$, OH, SH, $CH_2$ or $CH_3$, and L is $CH_3$, —$CH_2CH_3$ or $NH_2$.

or is a pharmaceutically acceptable salt or ester thereof

In another embodiment of the invention, pharmaceutical compositions are provided comprising a compound of the invention in combination with a pharmaceutically acceptable carrier. For those compounds that are orally active, oral formulations such as tablets, capsules, and the like are preferred. However, the invention also encompasses other types of formulations suited to various modes of administration, and includes, for example, injectable solutions, powders, suppositories, sprays, creams, ointments and the like.

In additional embodiments of the invention, methods of using the novel compounds are provided. A primary use of the compounds of the invention is in the treatment of cancer, particularly estrogen-dependent cancers such as breast and uterine cancer. The compounds are also useful to treat other estrogen-dependent disorders such as benign breast disease, endometriosis, osteoporosis, and the like. The compounds are additionally useful as diagnostic agents, particularly in MRI and MRS, in boron neutron capture therapy, and in fluorescence emission-based modalities.

DETAILED DESCRIPTION OF THE INVENTION

Figure 1:
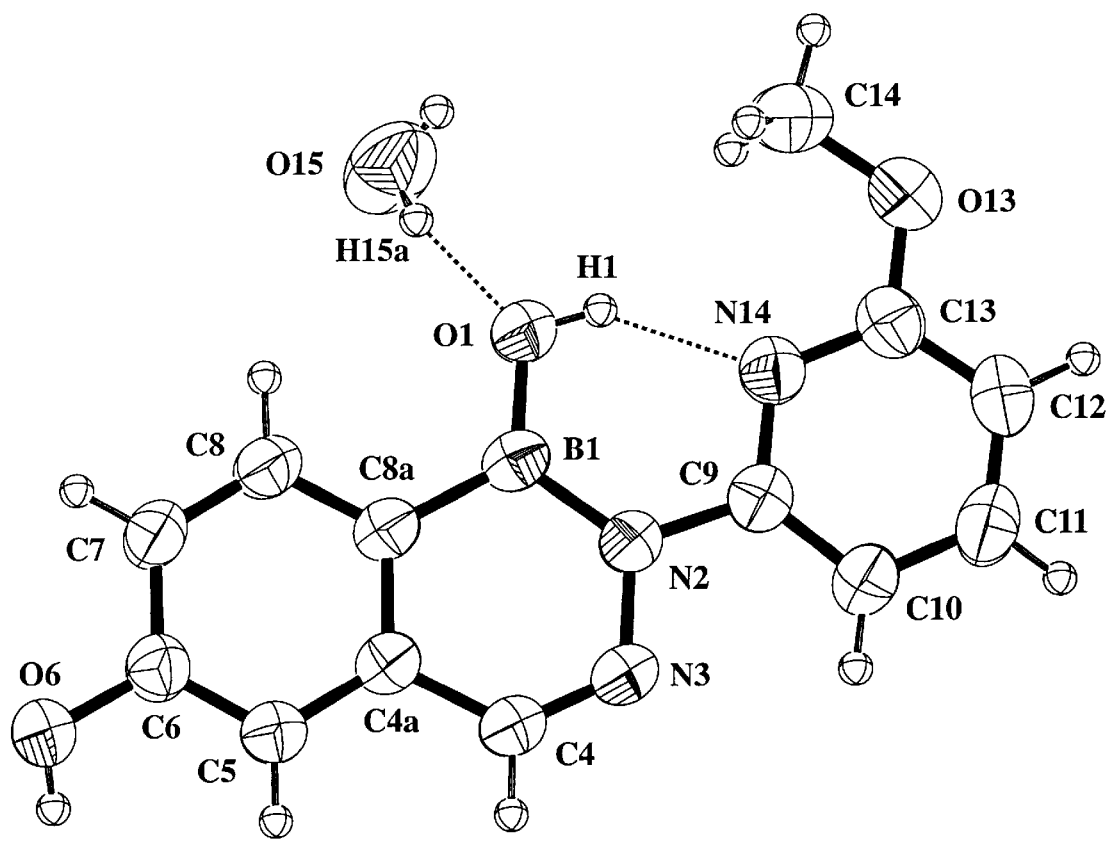
FIG. 1 shows the crystal structure of a compound of the invention, synthesized and characterized as described in Example 5.

Definitions and Nomenclature:

Before the present compounds, compositions and methods are disclosed and described, it is to be understood that this invention is not limited to specific molecular structures, methods of synthesis, pharmaceutical compositions, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a novel compound" in a composition means that more than one of the novel compounds can be present in the composition, reference to "a pharmaceutically acceptable carrier" includes combinations of such carriers, and the like. Similarly, reference to "a substituent" as in a compound substituted with "a substituent" includes the possibility of substitution with more than one substituent, wherein the substituents may be the same or different.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of one to six carbon atoms, preferably one to four carbon atoms. The term "cycloalkyl" as used herein refers to a cyclic hydrocarbon of from 3 to 8 carbon atoms, such as cyclopropyl, cyclobutyl, cyclopentyl, cyclohexyl, cycloheptyl and cyclooctyl.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of two to six carbon atoms, preferably two to four carbon atoms. The term "cycloalkenyl" intends a cyclic alkenyl group of three to eight, preferably five or six, carbon atoms.

The term "alkynyl" as used herein refers to a branched or unbranched hydrocarbon group of 2 to 24 carbon atoms containing at least one triple bond, such as ethynyl, n-propynyl, isopropynyl, n-butynyl, isobutynyl, octynyl, decynyl, and the like. Preferred alkynyl groups herein contain 2 to 12 carbon atoms. The term "lower alkynyl" intends an alkynyl group of two to six carbon atoms, preferably two to four carbon atoms.

The term "alkylene" as used herein refers to a difunctional branched or unbranched saturated hydrocarbon group of 1 to 24 carbon atoms, such as methylene, ethylene, n-propylene, n-butylene, n-hexylene, decylene, tetradecylene, hexadecylene, and the like. The term "lower alkylene" refers to an alkylene group of one to six carbon atoms, preferably one to four carbon atoms.

The term "alkenylene" as used herein refers to a difunctional branched or unbranched hydrocarbon group of 2 to 24 carbon atoms containing at least one double bond, such as ethenylene, n-propenylene, n-butenylene, n-hexenylene, and the like. The term "lower alkenylene" refers to an alkylene group of two to six carbon atoms, preferably two to four carbon atoms.

The term "alkoxy" as used herein intends an alkyl group bound through a single, terminal ether linkage; that is, an "alkoxy" group may be defined as —O-alkyl where alkyl is as defined above. A "lower alkoxy" group intends an alkoxy group containing one to six, more preferably one to four, carbon atoms.

The term "acyl" is used in its conventional sense to refer to a substituent alkyl-C—(O)— wherein alkyl is as defined above. The term "lower acyl" refers to an acyl group wherein the alkyl moiety of the group contains one to six, more preferably one to four, carbon atoms.

The term "aryl" as used herein, and unless otherwise specified, refers to an aromatic species containing 1 to 3 aromatic rings, either fused or linked, and either unsubstituted or substituted with 1 or more substituents typically selected from the group consisting of lower alkyl, lower alkoxy, halogen, and the like. Preferred aryl substituents contain 1 aromatic ring or 2 fused or linked aromatic rings. The term "arylene" refers to a difunctional aromatic species containing 1 to 3 aromatic rings substituted with 1 or more substituents as above. Preferred arylene substituents contain 1 aromatic ring (e.g., phenylene) or 2 fused or linked aromatic rings (e.g., biphenylylene).

The term "aralkyl" refers to an aryl group with an alkyl substituent. The term "aralkylene" refers to an arylene group with an alkyl substituent.

The term "alkaryl" refers to an alkyl group that has an aryl substituent. The term "alkarylene" refers to an alkylene group that has an aryl substituent.

The term "heterocyclic" refers to a five- or six-membered monocyclic structure or to an eight- to eleven-membered bicyclic heterocycle. The "heterocyclic" substituents herein may or may not be aromatic, i.e., they may be either heteroaryl or heterocycloalkyl. Each heterocycle consists of carbon atoms and from one to four, typically one to three, heteroatoms selected from the group consisting of nitrogen, oxygen and sulfur, typically nitrogen.

The term "halo" is used in its conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "hydrocarbyl" is used in its conventional sense to refer to a hydrocarbon group containing carbon and hydrogen, and may be aliphatic, alicyclic or aromatic, or may contain a combination of aliphatic, alicyclic and/or aromatic moieties. Aliphatic and alicyclic hydrocarbyl may be saturated or they may contain one or more unsaturated bonds, typically double bonds. The hydrocarbyl substituents herein generally contain 1 to 24 carbon atoms, more typically 1 to 12 carbon atoms, and may be substituted with various substituents and functional groups, or may be modified so as to contain ether and/or thioether linkages.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. Similarly, the phrase an "optionally present" double bond as indicated by a dotted line——— in the chemical formulae herein means that a double bond may or may not be present, and, if absent, a single bond is indicated.

The term "available" carbon or nitrogen atom refers to a carbon or nitrogen atom which is covalently bonded to one or more hydrogen atoms which can be replaced by a designated substituent without disrupting or destabilizing the remaining structure of the molecule.

By the terms "effective amount" or "pharmaceutically effective amount" of an agent as provided herein are meant a nontoxic but sufficient amount of the agent to provide the desired effect. As will be pointed out below, the exact amount required will vary from subject to subject, depending on the species, age, and general condition of the subject, the severity of the condition being treated, and the particular active agent and mode of administration, and the like. Thus, it is not possible to specify an exact "effective amount." However, an appropriate "effective" amount in any individual case may be determined by one of ordinary skill in the art using only routine experimentation.

By "pharmaceutically acceptable carrier" is meant a material which is not biologically or otherwise undesirable, i.e., the material may be administered to an individual along with the selected anti-estrogenic agent without causing any undesirable biological effects or interacting in a deleterious manner with any of the other components of the pharmaceutical composition in which it is contained. Similarly, a "pharmaceutically acceptable" salt or a "pharmaceutically acceptable" ester of a novel compound as provided herein is a salt or ester which is not biologically or otherwise undesirable.

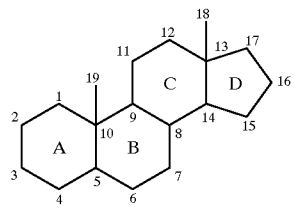

In describing the location of groups and substituents, the above numbering systems will be employed, to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

In these structures, the use of bold and dashed lines to denote particular conformation of groups again follows the IUPAC steroid-naming convention. The symbols "α" and "β" indicate the specific stereochemical configuration of a substituent at an asymmetric carbon atom in a chemical structure as drawn. Thus "α" denoted by a broken line, indicates that the group in question is below the general plane of the molecule as drawn, and "β" denoted by a bold line, indicates that the group at the position in question is above the general plane of the molecule as drawn.

In addition, the five- and six-membered rings of the steroid molecule are often designated A, B, C and D as shown.

The Novel Compounds:

In one embodiment, the invention is directed to novel compounds having the structural formula (I)

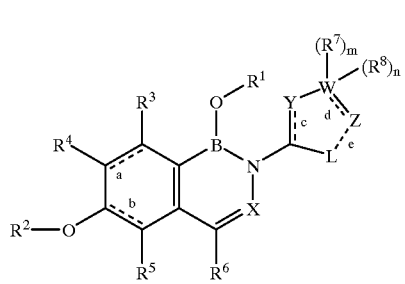

wherein:
a, b, c and d represent optional double bonds;
e represents an optional single bond; and
m and n are independently 0 or 1, with the proviso that if d is present as a double bond, one of m and n is 0.
$R^1$ is H, carbonyl, methylene or mono(lower alkyl)-substituted methylene, wherein, when carbonyl, methylene or mono(lower alkyl)-substituted methylene, $R^1$ is directly and covalently bound to Y. Preferably, $R^1$ is H or methylene.
$R^2$ is selected from the group consisting of H, lower alkyl, lower acyl, phenyl, benzyl, —C(O)-aryl and —$SO_2NH_2$. Preferably, $R^2$ is H or a hydroxyl-protecting group, and, most preferably, $R^2$ is H.
$R^3$ is H or lower alkyl, preferably H.
$R^4$ is selected from the group consisting of H, methoxy, halogen, cyano, —$CH_2CH$=$CH_2$, —CHO, —$NR^9R^{10}$ and —($CH_2$)$NR^9R^{10}$ wherein $R^9$ and $R^{10}$ are independently H or lower alkyl. Preferably, $R^4$ is H.
$R^5$ is selected from the group consisting of H, halogen, —$NO_2$, —CHO, —$CH_2CH$=$CH_2$, —$NR^9R^{10}$ and —($CH_2$)$NR^9R^{10}$ wherein $R^9$ and $R^{10}$ are independently H or lower alkyl. Preferably, $R^5$ is H.
$R^6$ is selected from the group consisting of H, hydroxyl, —$OR^{11}$ and —$SR^{11}$ wherein $R^{11}$ is lower alkyl, lower acyl or aryl. Preferably, $R^6$ is H.
One of $R^7$ and $R^8$ is H and the other is H, alkyl, alkenyl, alkynyl, alkoxy, acyl or acyloxy, or one of $R^7$ and $R^8$ is hydroxyl and the other is H, alkyl, alkenyl, alkynyl, acyl, or $R^7$ and $R^8$ together form =O. In preferred compounds, $R^7$ and $R^8$ are both H, or one of $R^7$ and $R^8$ is H and the other is hydroxyl, lower alkoxy or lower alkynyl, or $R^7$ and $R^8$ together form=O. In particularly preferred compounds, one of $R^7$ and $R^8$ is H and the other is hydroxyl or ethynyl, or $R^7$ and $R^8$ together form =O.
X is N, CH or $CR^{12}$ wherein $R^{12}$ is alkyl, aryl, —O-alkyl, —O -aryl, —S-alkyl or —S-aryl, wherein preferred $R^{12}$ moieties are lower alkyl, phenyl, —O-(lower alkyl), —O-phenyl, —S-(lower alkyl) and —S-phenyl. Preferably, X is N, CH or C(lower alkyl), and most preferably, X is N.
Y is N, NH, C or CH, and is optionally bound directly and covalently to $R^1$.
W is O, S, N or C, with the provisos that (1) if W is O or S, then d is absent and both m and n are 0, and (2) if W is N, then either (a) d is absent and one but not both of m and n is 0 or (b) d is present and m and n are both 0. Preferably, W is C.
When e is present, Z is N, O, S, CH or $CH_2$, with the proviso that W and Z are not both O and S, and L is $CH_2$, $CH_2$—$CH_2$, CH=CH or NH, while when e is absent, Z is NH, $NH_2$, OH, SH, $CH_2$ or $CH_3$, and L is $CH_3$, —$CH_2CH_3$ or $NH_2$. In preferred compounds, however, e is present.

Preferred compounds encompassed by structural formula (I) have the structure of formula (Ia)

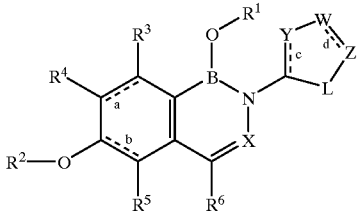

(Ia)

wherein:

a, b, c, d, $R^1$ through $R^6$, X and Y are as defined above for formula (I);

W and Z are N, O, S, CH or $CH_2$, with the proviso they are not both O and S; and L is $CH_2$, $CH_2$—$CH_2$, CH=CH or NH.

One group of compounds encompassed by structure of formula (Ia) has the structure of formula (II)

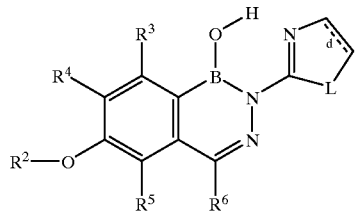

(II)

wherein d, $R^2$ through $R^6$ and L are as defined for compounds of formula (Ia).

Another group of compounds encompassed by structure of formula (Ia) has the structure of formula (III)

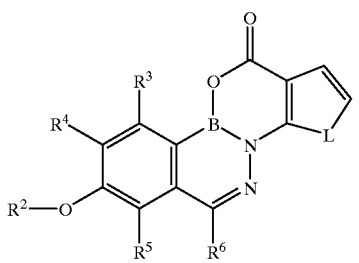

(III)

wherein $R^2$ through $R^6$ and L are as defined for compounds of formula (Ia).

An additional group of compounds encompassed by structure of formula (Ia) has the structure of formula (IV)

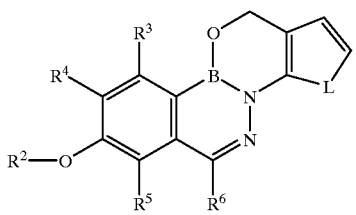

(IV)

wherein $R^2$ through $R^6$ and L are as defined for compounds of formula (Ia).

The compounds may be in the form of pharmaceutically acceptable salts or esters, or may be modified by appending one or more appropriate functionalities to enhance selected biological properties. Such modifications are known in the art and include those which increase biological penetration into a given biological system, increase oral bioavailability, increase solubility to allow administration by injection, and the like.

Salts of the compounds can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Acid addition salts are prepared from the free base (e.g., compounds having a neutral —$NH_2$ or cyclic amine group) using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preferred acid addition salts of the present compounds are the citrate, fumarate, succinate, benzoate and malonate salts.

Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Esters can be reconverted to the free acids, if desired, by using conventional hydrogenolysis or hydrolysis procedures.

Certain of the novel compounds are chiral in nature and can thus be in enantiomerically pure form or in a racemic mixture. In some cases, i.e., with regard to certain specific compounds illustrated herein, chirality is indicated. In other cases, it is not, and the invention is intended to encompass both the isomerically pure forms of the compounds shown and the racemic or diastereomeric mixtures thereof Pharmaceutical Compositions and Modes of Administration:

The pharmaceutical agents of the invention may be conveniently formulated into pharmaceutical compositions composed of one or more of the compounds in association with a pharmaceutically acceptable carrier. See *Remington: The Science and Practice of Pharmacy,* 19th Ed. (Easton, PA: Mack Publishing Co., 1995), which discloses typical carriers and conventional methods of preparing pharmaceutical compositions which may be used as described or modified to prepare pharmaceutical formulations containing the compounds of the invention. The compounds may also be administered in the form of pharmaceutically acceptable salts, or as pharmaceutically acceptable esters, as described in the preceding section.

The compounds may be administered orally, parenterally, transdermally, rectally, nasally, buccally, vaginally or via an implanted reservoir in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* referenced above.

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent is combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. A more recently revised approach for parenteral administration involves use of a slow release or sustained release system, such that a constant level of dosage is maintained. See, e.g., U.S. Pat. No. 3,710,795.

The compounds of the invention may also be administered through the skin or mucosal tissue using conventional transdermal drug delivery systems, wherein the agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferred formulations for vaginal drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

The specific ointment or cream base to be used, as will be appreciated by those skilled in the art, is one that will provide for optimum drug delivery. As with other carriers or vehicles, an ointment base should be inert, stable, nonirritating and nonsensitizing. Also preferred are vaginal suppositories. Suppositories may be formulated using conventional means, e.g., compaction, compression-molding or the like, and will contain carriers suited to vaginal drug delivery, typically a bioerodible material which provides for the desired drug release profile.

Formulations for buccal administration include tablets, lozenges, gels and the like. Alternatively, buccal administration can be effected using a transmucosal delivery system.

Utility:

The compounds of the invention find use as chemotherapeutic agents in the treatment of mammals suffering from a wide range of neoplasms, including cancers of the breast, uterus, prostate, colon, lung and the like; the compounds are particularly useful, however, in the treatment of estrogen-dependent cancers such as breast and uterine cancer. A patient in need of treatment is administered an amount of one or more of the above-described compounds which is effective to inhibit the growth of the cancer cell. The dosage requirements will vary with the route of administration, tumor type, the cytotoxic agent and formulation employed, and the particular subject being treated. Generally, however, dosage will be in the range of approximately 0.01 mg/kg/day to 10.0 mg/kg/day, more preferably in the range of about 1.0 mg/kg/day to 5.0 mg/kg/day. The effectiveness of the treatment is monitored by tumor biopsy, radiological methods, or blood enzyme levels, according to standard methods. In addition, the compounds of formula I may be administered in combination with a 5-$HT_3$ antagonist, such as ondansetron, granisetron or tropisetron, or other anti-emetic medicaments, for example, a dopamine antagonist such as metoclopramide. Additionally, a compound of formula I may be administered in combination with an anti-inflammatory corticosteroid, such as dexamethasone, or in combination with another chemotherapeutic agent such as cisplatin, dacarbazine (DTIC), dactinomycin, mechlorethamine, streptozocin, cyclophosphamide, carmustine (BCNU), lomustine (CCNU), doxorubicin, daunorubicin, procarbazine, mitomycin, cytarabine, etoposide, methotrexate, 5-fluorouracil, vinblastine, vincristine, bleomycin and chlorambucil.

The compounds of the invention are additionally useful in treating estrogen-dependent disorders other than estrogen-dependent cancers. Such estrogen-dependent disorders include, for example, endometriosis, benign breast disease, osteoporosis, and the like.

The present compounds are also useful in a method of boron neutron capture therapy (BNCT) for treating cancer, preferably brain gliomas and melanomas or gastrourinary cancers. A patient in need of BNCT is treated with an effective amount of one or more of the present compounds of formula I, and then exposed to thermal neutrons to generate $^7Li$ and $^4He$ thereby causing destruction of tumor cells. The compound administered contains at least a natural abundance, preferably at least about 99%, of boron-10. The preferred effective dose is about 0.1 to about 200 mg/kg of the compound of formula I to body weight of the patient. In addition, the dosage may be pulsed. Typically, the compounds of formula I are administered about 0.5 days to about 30 days before exposure to radiation. The neutron beam must deliver neutrons at the tumor site with an energy distribution sufficient to permit neutron capture by boron-10, generally about 0.4 eV to about 10 keV, as described in U.S. Pat. No. 5,144,026 to Gabel. The exposure to neutron beam is continued for a time sufficient to effect substantial tumor tissue destruction.

The compounds of the present invention may, in addition, be used as probes in a variety of diagnostic techniques, such as magnetic resonance imaging (MRI), magnetic resonance spectroscopy (MS) and fluorescence emission spectroscopy. MRI and MRS are noninvasive techniques for detecting and quantitating boron-10 and boron-11, such as in tumor tissue in a patient or in a sample from a patient. A patient is treated with one or more of the compounds of formula I of the present invention. The patient is then placed in an MRI instrument capable of detecting boron. The location and concentration of boron within the patient is then calculated. In the alternative, a sample from the patient is placed in an MRS instrument capable of detecting boron, and the presence and concentration of boron in the sample is determined.

Another diagnostic application of the compounds of formula I is their use as fluorescent probes in fluorescence emission spectroscopy. In fluorescence emission spectroscopy, a fluorescent molecule is irradiated with electromagnetic radiation having a known wavelength, including ultra violet and visible light. The fluorescent molecule therein absorbs the energy and then emits the energy as light having a wavelength longer than the absorbed light. The amount of emitted light is determined by a photodetector. Generally, the radiation is directed into the sample cell through an optical light filter or monochromator and the filter is set for a specific combination of excitation and emission wavelengths. One method for the monitoring chemical tracers by fluorescence emission spectroscopy is described in U.S. Pat. No. 4,992,380 issued to Moriarity et al. Thus, a fluorescent compound of formula I incorporating a boron is administered to a patient. A sample from the patient is then obtained, the sample irradiated with electromagnetic radiation, and fluorescence detected to detect and quantitate boron in the sample.

Synthesis:

The compounds of the invention can be synthesized, for example, by the route shown below:

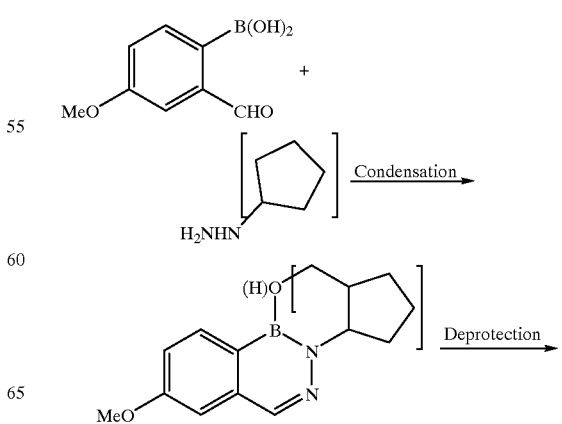

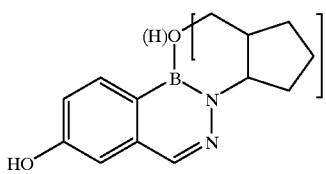

In general, the available 2-formyl-4-methoxybenzeneboronic acid, appropriately substituted on the aromatic ring, serves as the A-ring precursor. The compound is condensed with an appropriate azolyl or cycloalkanyl hydrazine to yield, in a single step, the 3-hydroxyl-protected compound of formula I. Deprotection yields the final product. Compounds of formula (I) wherein $R^1$ is a methylene group can be synthesized by reduction of the lactone before deprotection. In this scheme, the moiety "X" of formulae (I) and (Ia) is N. For compounds wherein X is carbon-containing, e.g., wherein X is CH, a variation on the aforementioned scheme may be used, as follows:

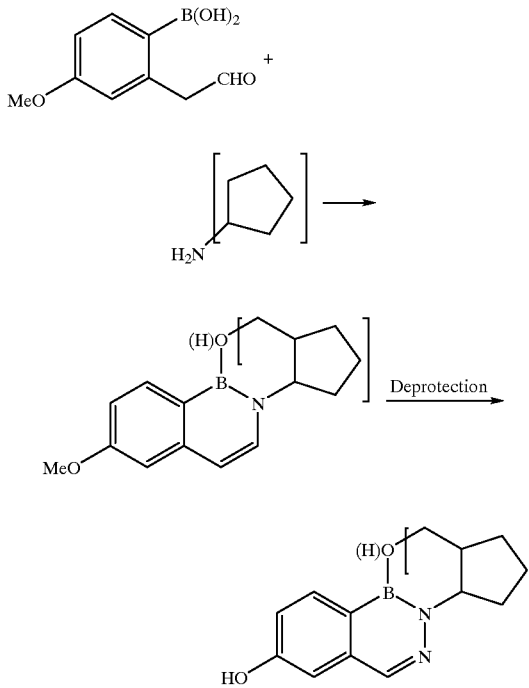

Variations on these basic synthetic schemes to provide other compounds within the scope of the invention will be apparent to those skilled in the art.

Experimental:

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All patents, patent applications, journal articles and other references mentioned herein are incorporated by reference in their entireties.

EXAMPLE 1

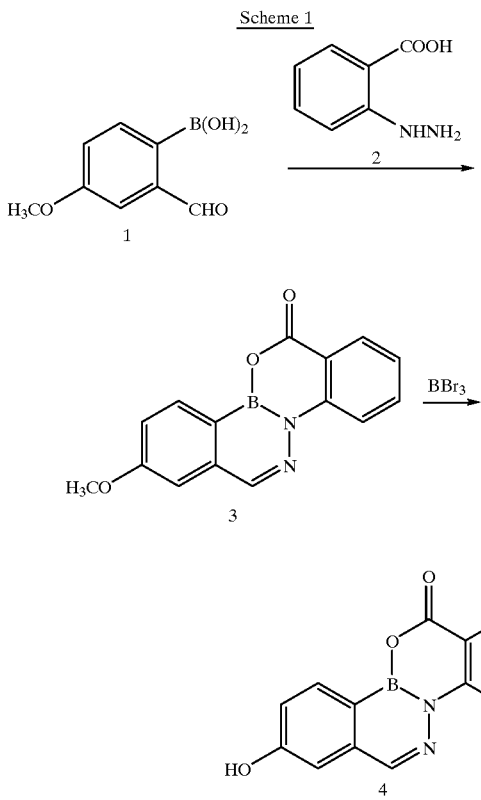

Synthesis of 1,2-dihydro-1,6-dihydroxy-2-(2-carboxyphenyl)-2,3,1-benzodiazaborine lactone (compound 4):

A solution of 2-formyl-4-methoxybenzeneboronic acid (compound 1; 1.8 g, 10 mmol) in 20 mL of absolute ethanol was added to a hot solution of the hydrochloride salt of 2-hydrazinobenzoic acid (compound 2; 2.07 g, 11 mmol) in 10 mL of water. A copious precipitate formed immediately. The mixture was diluted with 50 mL of absolute ethanol and was then suction filtered. After washing with a small amount of absolute ethanol and drying in vacuo, 1.77 g (64%) of the methoxy precursor 3 was obtained, mp 240–242° C. (ethanol). $^1$H NMR (CDCl$_3$) δ 8.39 (s, 1, H4), 8.38 (bs, 1), 8.34 (d, J=5.4 Hz, 1), 8.31 (pseudo-t, 2), 7.80 (pseudo-t, 1), 7.37 (d of d, 1), 7.33 (d of d, 1), 7.21 (d, J=2.3 Hz, 1), 3.97 (s, 3, OCH$_3$). Low-resolution DCI mass spectrum, m/z 279 (100%, MH$^+$). Exposure of this to BBr$_3$ in CH$_2$Cl$_2$ solution at 23° C. overnight effected the removal of the phenolic protecting group and gave 4: $^1$H NMR ((CD$_3$)$_2$SO) δ 10.52 (s, 1, PhOH), 8.53 (s, 1, H4), 8.26 (d, 1), 8.12 (d, 1), 8.08 (d, 1), 8.86 (pseudo-t, 1), 7.47 (pseudo-t, 1), 7.29 (s, 1), 7.27 (d, 1). Low-resolution DCI mass spectrum, m/z 265 (100%, MH$^+$).

EXAMPLE 2

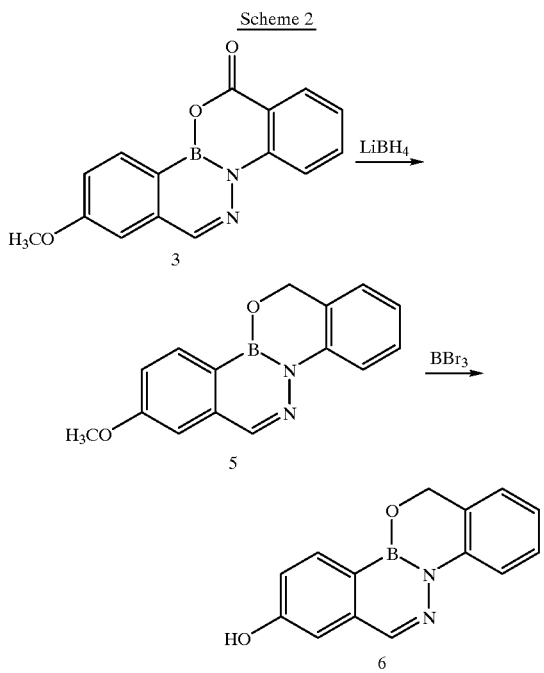

Synthesis of 1,2-Dihydro-1,6-dihydroxy-2-[2-(hydroxymethyl)phenyl]-2,3,1-benzodiazaborine anhydride (compound 6):

A solution of 3 (556 mg, 2 mmol) in 35 mL of anhydrous THF under argon was treated with solid LiBH$_4$ (200 mg, excess) and the reduction mixture was stirred at 23° C. for 24 h. After adding 2 mL of EtOAc to quench excess borohydride, the mixture was treated with water and was extracted several times with CH$_2$Cl$_2$. The combined organic layers were dried (Na$_2$SO$_4$) and then were rotary evaporated to a residue which proved to be a binary mixture by TLC (CH$_2$Cl$_2$ as eluent). Elution of a CH$_2$Cl$_2$ solution of this mixture through a short SiO$_2$ column afforded a small sample of the methoxy precursor, compound 5, mp 122–124° C. (EtOH). $^1$H NMR (CDCl$_3$) δ 8.10 (s, 1, H4), 8.01 (d, J=8.5 Hz, 1), 7.93 (d, J=8.3 Hz, 1), 7.35 (d of d, 1), 7.32 (pseudo-t, 1), 7.19 (d of d, J=2.6, 8.4 Hz, 1), 7.09 (d, J=2.4 Hz, 1), 7.05 (bs, 1), 5.32 (s, 2, CH$_2$), 3.93 (s, 3, OCH$_3$). Low-resolution DCI mass spectrum, m/z 265 (100%, MH$^+$). Exposure of this to BBr$_3$ effected the removal of the phenolic protecting group, giving 6.

EXAMPLE 3

Scheme 3

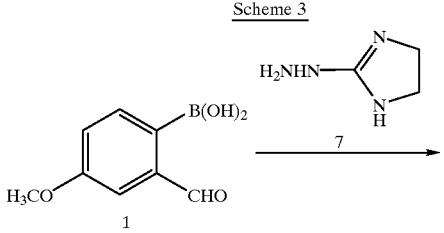

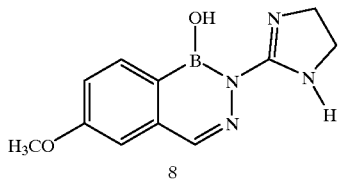

Synthesis of 1,2-dihydro-1,6-dihydroxy-2-(imidazolidinyl)-2,3,1-benzodiazaborine (compound 8):

A solution of 1 (450 mg, 2.5 mmol) and 2-hydrazinoimidazoline hydrobromide (compound 7, 500 mg, 2.75 mmol) in 7.5 mL of absolute ethanol was treated with a solution of 100 mg of NaOH in 1.5 mL of water. The suspension of the precipitate generated was stirred at 23° C. for 24 h, after which the mixture was suction filtered and the solid washed with a small amount of ethanol. Drying in vacuo afforded 470 mg (77%) of 8 as a white microcrystalline anhydrous dimer: mp 281–282° C. (ethanol). $^1$H NMR ((CD$_3$)$_2$SO) δ 7.57 (s, 1, exchanges upon addition of D$_2$O, OH), 7.49 (s, 1, H4), 7.38 (d, 1), 6.96 (s, 1), 6.94 (d, 1), 3.78 (s, 3, OCH$_3$), 3.32 (t, 1), 3.26 (t, 1), 2.97 (pseudo-q, 1), 2.73 (pseudo-q, 1). Low-resolution DCI mass spectrum, m/z 471 (100%, anhydrous dimer MH$^+$).

EXAMPLE 4

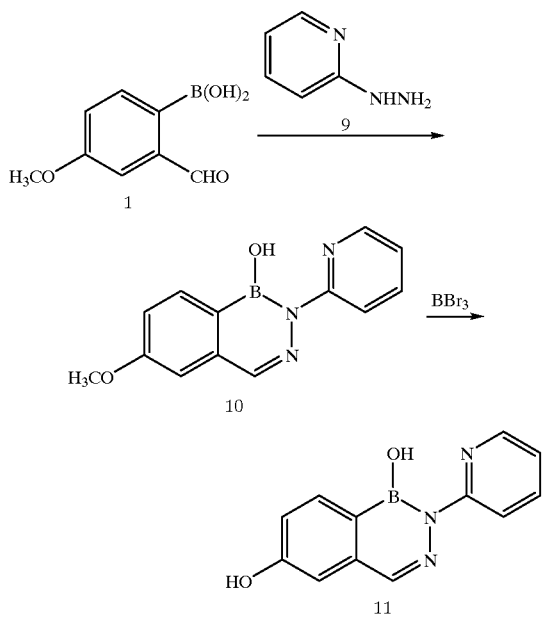

Synthesis of 1,2-dihydro-1,6-dihydroxy-2-(6-pyridinyl)-2,3,1-benzodiazaborine (compound 11 in Scheme 4):

A solution of 1 (450 mg, 2.5 mmol) in 2.5 mL of absolute ethanol was treated with a solution of 2-hydrazinopyridine (compound 9; 300 mg, 2.75 mmol) in 2.5 mL of ethanol, and the reaction mixture was allowed to stand at 23° C. overnight. The precipitate that formed was collected by suction filtration, washed with a small amount of ethanol, and was dried in vacuo, giving 400 mg (63%) of the methoxy precursor 10 as a white microcrystalline anhydrous dimer: compound 10, mp 256–258.5° C. (EtOH). $^1$H NMR ((CD$_3$)$_2$SO) δ 7.92 (s, 1, H4), 7.86 (d, 1), 7.71 (pseudo-t, 1), 7.43 (d, J=8.2 Hz, 1), 7.20 (s, 1), 7.02 (d of d, 1), 6.87 (d, 1), 6.64 (pseudo-t, 1), 3.85 (s, 3, OCH$_3$). Low-resolution DCI mass spectrum, m/z 489 (61%, anhydrous dimer MH$^+$), 254 (100%, MH$^+$). Exposure of this to BBr$_3$ effected the removal of the phenolic protecting group, giving 11.

EXAMPLE 5

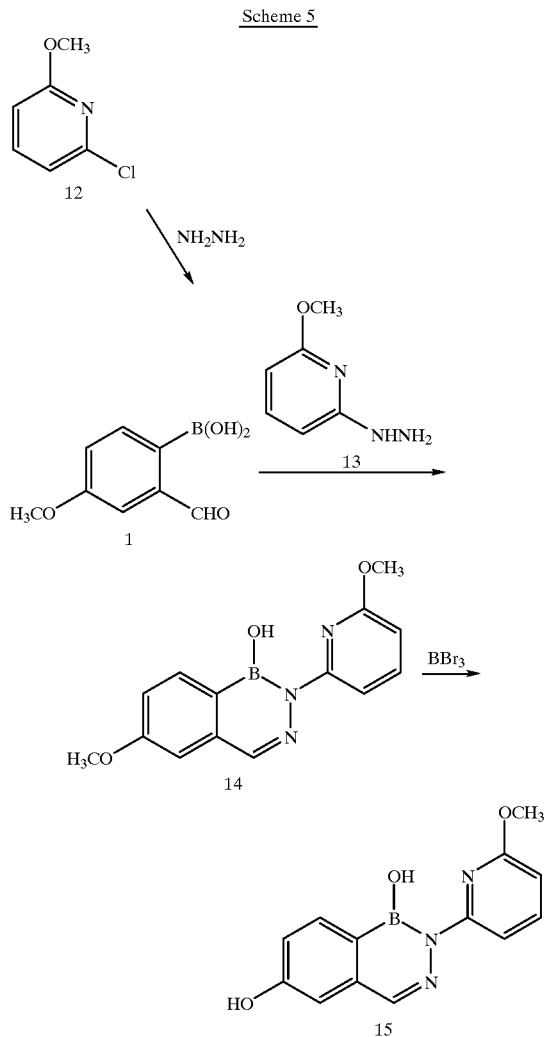

Scheme 5

Synthesis of 1,2-dihydro-1,6-dihydroxy-2-(2-methoxy-6-pyridinyl)-2,3,1-benzodiazaborine (compound 15):

A mixture of 2-chloro-6-methoxypyridine (compound 12; 2.87 g, 20 mmol) and anhydrous hydrazine (11 mL, excess) was heated under argon on a steam bath overnight. The mixture was allowed to cool to 23° C. and then was extracted with Et$_2$O (10×10 mL). The combined ether extracts were rotary evaporated to afford 1.58 g (57%) of 2-hydrazino-6-methoxypyridine 13 as a yellow liquid that was ~95% pure by NMR: $^1$H NMR (CDCl$_3$) δ 7.38 (pseudo-t, 1), 6.20 (d, J=8.0 Hz, 1), 6.09 (d, J=8.0 Hz, 1), 5.71 (bs, 1, exchanges upon addition of D$_2$O, NH), 3.84 (s, 3, OCH$_3$), 3.1 (bs, 2, exchanges upon addition of D$_2$O, NH$_2$). A solution of this hydrazine (1.58 g, 11 mmol) in 10 mL of absolute ethanol was combined with a solution of 1 (1.8 g, 10 mmol) in 20 mL of absolute ethanol, and the reaction mixture produced a precipitate within several minutes. The mixture was allowed to stand at 23° C. overnight. The solid was collected by suction filtration, washed with a small amount of ethanol, and was dried in vacuo, giving 1.65 g of the methoxy precursor 14. An additional 510 mg of this precipitated from the filtrate after it had been concentrated on a rotary evaporator to a small volume. Combined yield: 2.15 g (76%): mp 161–162° C. (ethanol). $^1$H NMR ((CD$_3$)$_2$SO) δ 10.45 (s, 1, exchanges upon addition of D10, OH), 8.25 (s, 1, H4), 8.04 (d, J=8.2 Hz, 1), 7.88 (pseudo-t, 1), 7.54 (d, J=8.2 Hz, 1), 7.36 (s, 1), 7.26 (d, J=8.25 Hz, 1), 6.68 (d, J=7.9 Hz, 1), 6.64 (pseudo-t, 1), 3.92 (s, 3, OCH$_3$), 3.90 (s, 3, OCH$_3$). Low-resolution DCI mass spectrum, m/z 284 (100%, MH$^+$). Exposure of this compound to molten C$_5$H$_5$N∘HCl for 10 min effected removal of the hydroxy pyridine protecting group only, by $^1$H NMR. Exposure to BBr$_3$ in CH$_2$Cl$_2$ solution at 23° C. overnight effected the removal of the phenolic protecting group only, giving 15: mp 198–199° C. (ethanol). $^1$H NMR ((CD$_3$)$_2$SO) δ 8.17 (s, 1, H4), 7.98 (d, 1), 7.88 (pseudo-t, 1), 7.54 (d, 1), 7.12 (m, 3), 6.67 (d, 1), 3.92 (s, 3, OCH$_3$). Low-resolution DCI mass spectrum, m/z 270 (100%, MH$^+$). X-ray quality crystals of 15 were grown from absolute ethanol and a crystal structure determination was made; the crystal structure of the compound is shown in FIG. 1.

EXAMPLE 6

ANTIPROLIFERATIVE ASSAY PROCEDURE

MCF-7 cells were obtained from the American Type Culture Collection (ATCC, Rockville, Md.). Exponentially growing cells were plated (96-well plates) in MEM (minimal essential medium) containing NaHCO$_3$, CCD (charcoal-coated dextran)-stripped 10% FCS (fetal calf serum), and glycine. Cultures were incubated at 37° C. for 1 day, then treated with target by replacing the medium with 100 μL MEM containing supplements and target (3 wells at each of 5 concentrations). The relative effect of each concentration was compared to that of β-estradiol (positive control) by the alamar Blue™ assay (Biosource International), in which the dye is reduced by cellular mitochondrial enzymes to a soluble fluorophore with an intensity directly proportional to cell number. After cultures were incubated with target, alamar Blue™ diluted to 20% in MEM was added (100 μL/well) and cells were incubated for about 4 h, until a color change indicated sufficient amounts of reduced dye for quantitation. Relative cell number was evaluated directly from the plates by fluorimetry (560 nm excitation, 590 nm detection) on a Millipore 2300 CytoFluor. The concentration at which 50% effectiveness is seen (EC$_{50}$) was calculated from statistically significant, reproducible effects. Statistical analysis was performed using JMP software (SAS Institute). Results are set forth in Table 1:

TABLE 1

| Compound | Concentration | % Inhibition |
|---|---|---|
| 4 | 10$^{-9}$ | 0 |
| 4 | 10$^{-8}$ | 6 |
| 4 | 10$^{-7}$ | 2 |
| 4 | 10$^{-6}$ | 4 |
| 4 | 10$^{-5}$ | 13 |
| 11 | 10$^{-9}$ | 5 |
| 11 | 10$^{-8}$ | 8 |
| 11 | 10$^{-7}$ | 8 |
| 11 | 10$^{-6}$ | 10 |
| 11 | 10$^{-5}$ | 55 |
| 15 | 10$^{-9}$ | 0 |
| 15 | 10$^{-8}$ | 0 |
| 15 | 10$^{-7}$ | 0 |
| 15 | 10$^{-6}$ | 3 |

TABLE 1-continued

| Compound | Concentration | % Inhibition |
| --- | --- | --- |
| 15 | $10^{-5}$ | 62 |
| tamoxifen | $10^{-9}$ | 0 |
| tamoxifen | $10^{-8}$ | 5 |
| tamoxifen | $10^{-7}$ | 29 |
| tamoxifen | $10^{-6}$ | 54 |
| tamoxifen | $10^{-5}$ | 95 |

What is claimed is:

1. A compound having the structural formula

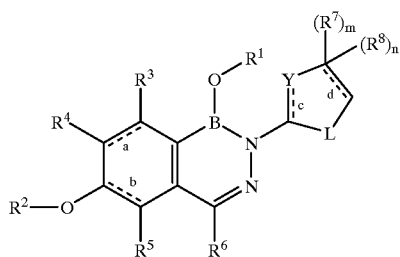

wherein:

a, b, c and d represent optional double bonds;

m and n are independently 0 or 1, with the proviso that if d is present as a double bond, one of m and n is 0;

$R^1$ is H, methylene or mono(lower alkyl)-substituted methylene, wherein, when methylene or mono(lower alkyl)-substituted methylene, $R^1$ is directly and covalently bound to Y;

$R^2$ is selected from the group consisting of H, lower alkyl, lower acyl, phenyl, benzyl, —C(O)-aryl and —SO$_2$NH$_2$;

$R^3$ is H or lower alkyl;

$R^4$ is selected from the group consisting of H, methoxy, halogen, cyano, —CH$_2$CH=CH$_2$, —CHO, —NR$^9$R$^{10}$ and —(CH$_2$)NR$^9$R$^{10}$ wherein $R^9$ and $R^{10}$ are independently H or lower alkyl;

$R^5$ is selected from the group consisting of H, halogen, —NO$_2$, —CHO, —CH$_2$CH=CH$_2$, —NR$^9$R$^{10}$ and —(CH$_2$)NR$^9$R$^{10}$ wherein $R^9$ and $R^{10}$ are independently H or lower alkyl;

$R^6$ is selected from the group consisting of H, hydroxyl, —OR$^{11}$ and —SR$^{11}$ wherein $R^{11}$ is lower alkyl, lower acyl or aryl;

one of $R^7$ and $R^8$ is H and the other is H, alkyl, alkenyl, alkynyl, alkoxy, acyl or acyloxy, or one of $R^7$ and $R^8$ is hydroxyl and the other is H, alkyl, alkenyl, alkynyl, acyl, or $R^7$ and $R^8$ together form =O;

Y is C or CH, and is optionally bound directly and covalently to $R^1$; and

L is CH$_2$, CH$_2$—CH$_2$, or CH=CH;

and pharmaceutically acceptable salts and esters thereof.

2. The compound of claim 1, wherein a and b both represent double bonds.

3. The compound of claim 2, wherein:

$R^1$ is H or methylene;

$R^2$, $R^4$, $R^5$ and $R^6$ are H;

$R^3$ is H or lower alkyl; and one of $R^7$ and $R^8$ is H and the other is H, hydroxyl, lower alkoxy or lower alkynyl, or $R^7$ and $R^8$ together form =O.

4. The compound of claim 3, wherein $R^1$ is H, $R^3$ is H, and one of $R^7$ and $R^8$ is H and the other is hydroxyl or ethynyl, or $R^7$ and $R^8$ together form =O.

5. A compound having the structural formula

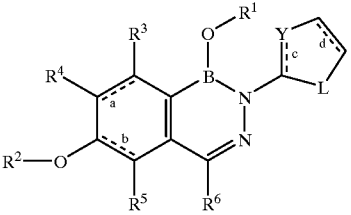

wherein:

a, b, c and d represent optional double bonds;

$R^1$ is H, methylene or mono(lower alkyl)-substituted methylene, wherein, when methylene or mono(lower alkyl)-substituted methylene, $R^1$ is directly and covalently bound to Y;

$R^2$ is selected from the group consisting of H, lower alkyl, lower acyl, phenyl, benzyl, —(O)-aryl and —SO$_2$NH$_2$;

$R^3$ is H or lower alkyl;

$R^4$ is selected from the group consisting of H, methoxy, halogen, cyano, —CH$_2$CH=CH$_2$, —CHO, —NR$^9$R$^{10}$ and —(CH$_2$)NR$^9$R$^{10}$ wherein $R^9$ and $R^{10}$ are independently H or lower alkyl;

$R^5$ is selected from the group consisting of H, halogen, —NO$_2$, —CHO, —CH$_2$CH=CH$_2$, —NR$^9$R$^{10}$ and —(CH$_2$)NR$^9$R$^{10}$ wherein $R^9$ and $R^{10}$ are independently H or lower alkyl;

$R^6$ is selected from the group consisting of H, hydroxyl, —OR$^{11}$ and —SR$^{11}$ wherein $R^{11}$ is lower alkyl, lower acyl or aryl;

Y is C or CH, and is optionally bound directly and covalently to $R^1$; and

L is CH$_2$, CH$_2$—CH$_2$, or CH=CH;

and pharmaceutically acceptable salts and esters thereof.

6. The compound of claim 5, wherein a and b both represent double bonds.

7. The compound of claim 6, wherein:

$R^1$ is H or methylene;

$R^2$, $R^4$, $R^5$ and $R^6$ are H; and $R^3$ is H or lower alkyl.

8. The compound of claim 7, wherein $R^1$ and $R^3$ are H.

9. A compound having the structural formula (IV)

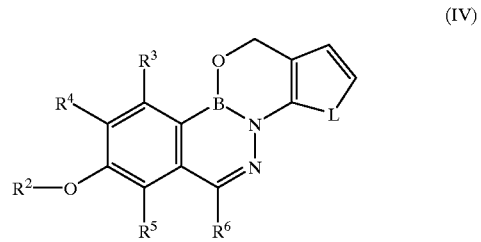

(IV)

wherein:

$R^2$ is selected from the group consisting of H, lower alkyl, lower acyl, phenyl, benzyl, —(O)-aryl and —SO$_2$NH$_2$;

$R^3$ is H or lower alkyl;

$R^4$ is selected from the group consisting of H, methoxy, halogen, cyano, —CH$_2$CH=CH$_2$, —CHO, —NR$^9$R$^{10}$ and —(CH$_2$)NR$^9$R$^{10}$ wherein R$^9$ and R$^{10}$ are independently H or lower alkyl;

R$^5$ is selected from the group consisting of H, halogen, —NO$_2$, —CHO, —CH$_2$CH=CH$_2$, —NR$^9$R$^{10}$ and —(CH$_2$)NR$^9$R$^{10}$ wherein R$^9$ and R$^{10}$ are independently H or lower alkyl;

R$^6$ is selected from the group consisting of H, hydroxyl, —OR$^{11}$ and —SR$^{11}$ wherein R$^{11}$ is lower alkyl, lower acyl or aryl; and L is CH$_2$, CH$_2$—CH$_2$, CH=CH or NH.

10. The compound of claim 9 wherein:

R$^1$ is H or methylene;

R$^2$, R$^4$, R$^5$ and R$^6$ are H; and

R$^3$ is H or lower alkyl.

11. The compound of claim 10, wherein R$^1$ and R$^3$ are H.

12. The compound of claim 10, wherein L is CH$_2$.

13. A. The compound of claim 11, wherein L is CH$_2$.

14. A pharmaceutical composition comprising a therapeutically effective amount of the compound of claim 1 in combination with a pharmaceutically acceptable carrier.

15. A pharmaceutical composition comprising a therapeutically effective amount of the compound of claim 5 in combination with a pharmaceutically acceptable carrier.

16. A pharmaceutical composition comprising a therapeutically effective amount of the compound of claim 9 in combination with a pharmaceutically acceptable carrier.

17. The pharmaceutical composition of claim 14, in unit dosage form.

18. The pharmaceutical composition of claim 17, wherein the pharmaceutically acceptable carrier is suitable for oral drug administration.

19. A method for treating an individual with an estrogen-dependent disorder, comprising administering to the individual a therapeutically effective amount of the compound of claim 1.

20. A method for treating an individual with an estrogen-dependent disorder, comprising administering to the individual a therapeutically effective amount of the compound of claim 5.

21. A method for treating an individual with an estrogen-dependent disorder, comprising administering to the individual a therapeutically effective amount of the compound of claim 9.

22. The method of any one of claims 19–21, wherein the estrogen-dependent disorder is breast cancer.

23. A method for detecting tumor cells in a mammalian individual, comprising administering to the individual an effective tumor-detecting amount of the compound of claim 1; and detecting any of said compound associated with and retained by tumor cells present in the mammalian individual.

24. The method of claim 23, wherein the detecting is carried out using $^{11}$B magnetic resonance spectroscopy.

25. The method of claim 23, wherein the detecting is carried out using $^{11}$B magnetic resonance imaging.

26. At A method for performing boron neutron capture therapy, comprising: administering to a patient an effective amount of the compound of claim 1; locating a cancerous tumor in the individual by scanning the patient with a device capable of detecting the location and extent of boron uptake within the patient's body; irradiating the tumor so located with thermal neutrons to permit neutron capture by $^{10}$B, the decay of which into $^7$Li and $^4$He causes destruction of tumor cells.

* * * * *